United States Patent

Behler et al.

Patent Number: 5,688,759
Date of Patent: Nov. 18, 1997

[54] NITROGEN-FREE ANIONIC CONDITIONING FORMULATIONS

[75] Inventors: Ansgar Behler, Bottrop; Günther Uphues, Monheim; Bernd Wahle, Kaarst, all of Germany

[73] Assignee: Henkel Kommanditgesellschaft auf Aktien, Duesseldorf, Germany

[21] Appl. No.: 619,470

[22] PCT Filed: Sep. 14, 1994

[86] PCT No.: PCT/EP94/03075

§ 371 Date: Mar. 22, 1996

§ 102(e) Date: Mar. 22, 1996

[87] PCT Pub. No.: WO95/08613

PCT Pub. Date: Mar. 30, 1995

[30] Foreign Application Priority Data

Sep. 22, 1993 [DE] Germany ............... 43 32 187.9

[51] Int. Cl.⁶ .................. C11D 1/12; C11D 1/16; C11D 1/24; C11D 1/28

[52] U.S. Cl. .............. 510/526; 510/426; 510/437; 510/327; 510/328; 510/491; 510/495; 510/521; 510/515; 510/522; 510/536; 510/537; 8/150.5; 8/156; 560/1; 560/4; 560/26; 560/33

[58] Field of Search ................. 510/426, 437, 510/327, 328, 491, 495, 521, 526, 515, 522, 536, 537; 8/150.5, 156; 560/1, 4, 26, 33

[56] References Cited

U.S. PATENT DOCUMENTS

| | | | |
|---|---|---|---|
| 3,808,200 | 4/1974 | Bistline et al. | 260/234 R |
| 5,117,032 | 5/1992 | Fabry et al. | 558/34 |

FOREIGN PATENT DOCUMENTS

| | | |
|---|---|---|
| 0494769 | 7/1992 | European Pat. Off. . |
| 1056576 | 5/1959 | Germany . |
| 4031268 | 4/1992 | Germany . |
| 50091607 | 7/1975 | Japan . |
| 2169894 | 7/1986 | United Kingdom . |
| WO 9109009 | 6/1991 | WIPO . |
| WO 9118871 | 12/1991 | WIPO . |

OTHER PUBLICATIONS

Seifen–Öle–Fete–Wachse, 117, 287–292 and 690–694 (1991).

J. Falbe (ed.), "Surfactants in Consumer Products", Springer, Verlag, Berlin–Heidelberg, 1987, p. 61.

*Primary Examiner*—Paul Lieberman
*Assistant Examiner*—Charles I. Boyer
*Attorney, Agent, or Firm*—Ernest G. Szoke; Wayne C. Jaeschke; Henry E. Millson, Jr.

[57] ABSTRACT

Nitrogen-free anionic conditioning formulations containing sulfated polyol fatty acid esters corresponding to formula (I):

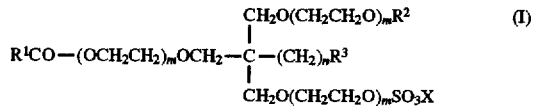

in which $R^1CO$ is a linear or branched, saturated or unsaturated acyl radical containing 6 to 22 carbon atoms, $R^2$ represents hydrogen, an $OCR^1$ group or an $SO_3X$ group, $R^3$ is hydrogen or an $(OCH_2CH_2)_mOR^2$ group, n is 0 or a number of 1 to 5, m is 0 or a number of 1 to 10, and X is an alkali metal, alkaline earth metal, ammonium, alkylammonium, alkanolammonium or glucammonium ion.

19 Claims, No Drawings

NITROGEN-FREE ANIONIC CONDITIONING FORMULATIONS

BACKGROUND OF THE INVENTION

1. Field of the Invention

This invention relates to nitrogen-free anionic conditioning formulations containing sulfated polyol fatty acid esters and to the use of the sulfated polyol fatty acid esters for the production of these formulations.

2. Statement of Related Art

Cationic or pseudocationic compounds are predominantly used for softening textiles, yarns and fibers and also in the finishing of leather and in papermaking. Important representatives of this group are, for example, distearyl dimethyl ammonium chloride (DSDMAC), quaternized difatty acid alkanolamine ester salts or reaction products of fatty acids with polyamines, for example aminoethyl ethanolamine. Although these compounds have excellent conditioning properties, the biological degradability and the sensitizing potential of a number of products are not entirely satisfactory (cf. Seifen-Öle-Fette-Wachse, 117, 287 and 690 (1991)). In addition, the—admittedly more theoretical—possibility that, starting out from cationic surfactants, traces of nitrosamines could be formed in water-based formulations leads to a market need for conditioning formulations which are free from nitrogen-containing compounds.

Numerous anionic compounds which also have conditioning properties coupled with good biodegradability are in fact known from the extensive prior art on the subject of conditioners and fabric softeners. Unfortunately, the performance of hitherto known anionic conditioners is so poor that, despite their ecotoxicological advantages, they have not yet been used in commercial products.

In addition, the use of nonionic surfactants or fatty compounds, for example pentaerythritol difatty acid esters, in combination with small quantities of fatty alcohol or fatty amine polyglycol ethers as a raw material for the production of fabric softeners is claimed in EP-B 0 494 769 (Colgate).

Now, the problem addressed by the present invention was to provide new nitrogen-free anionic conditioning formulations which would be free from the disadvantages mentioned above.

DESCRIPTION OF THE INVENTION

The present invention relates to nitrogen-free anionic conditioning formulations containing sulfated polyol fatty acid esters corresponding to formula (I):

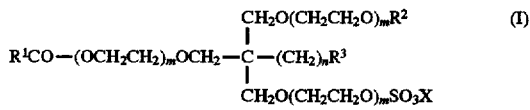

in which $R^1CO$ is a linear or branched, saturated and/or unsaturated acyl radical containing 6 to 22 carbon atoms, $R^2$ represents hydrogen, an $OCR^1$ group or an $SO_3X$ group, $R^3$ is hydrogen or an $(OCH_2CH_2)_mOR^2$ group, n is 0 or a number of 1 to 5, m is 0 or a number of 1 to 10 and X is an alkali metal, alkaline earth metal, ammonium, alkylammonium, alkanolammonium or glucammonium ion.

It has surprisingly been found that sulfated polyol fatty acid esters have very good conditioning properties, are readily biodegradable and, hence, have all the necessary qualifications to be successfully used in conditioners and fabric softeners.

Polyol Fatty Acid Esters

Particularly suitable starting materials for the production of the sulfated polyol fatty acid esters are fatty acid esters of trimethylol propane and pentaerythritol or fatty acid esters of adducts of 1 to 10 moles of ethylene oxide with these polyols. These esters are of course largely present in the form of their partial esters, i.e. a significant percentage of free hydroxyl groups at which sulfation can take place is present. Trimethylol propane or pentaerythritol difatty acid esters or mixtures containing an average of two fatty acid groups per molecule are preferred on performance grounds. Advantageous fatty acid components are, above all, $C_{12-18}$ fatty acids, but especially technical $C_{16/18}$ tallow fatty acids which may have iodine values in the range from 0 to 40. Accordingly, the preferred starting materials are ditallow fatty acid esters of trimethylol propane and pentaerythritol.

Sulfation

The sulfation of the polyol fatty acid esters may be carried out by any of the known methods for the sulfation of fatty acid lower alkyl esters (J. Falbe (ed.), "Surfactants in Consumer Products", Springer Verlag, Berlin-Heidelberg, 1987, page 61) using reactors operating on the falling-film principle. Suitable sulfating agents are chlorosulfonic acid and, in particular, gaseous sulfur trioxide. Gaseous sulfur trioxide is normally diluted with an inert gas, preferably air or nitrogen, and used in the form of a gas mixture which contains the sulfating agent in a concentration of 1 to 8% by volume and, more particularly, 2 to 5% by volume.

The molar ratio of polyol fatty acid ester to sulfating agent may be from 1:0.5 to 1:2.5 and is preferably from 1:0.95 to 1:1.5. The sulfation reaction is normally carried out at temperatures of 20° to 98° C. With regard to the viscosity of the starting materials on the one hand and the color quality of the resulting sulfation products on the other hand, it has proved to be optimal to carry out the reaction at a temperature in the range from 80° to 95° C.

The acidic sulfation products formed during the sulfation reaction are stirred into aqueous bases, neutralized and adjusted to a pH value of 6.5 to 8.5. Suitable bases for the neutralization step are alkali metal hydroxides, such as sodium, potassium and lithiumhydroxide, alkaline earth metal oxides and hydroxides, such as magnesium oxide, magnesium hydroxide, calcium oxide and calcium hydroxide, ammonia, mono-, di- and tri-$C_{2-4}$-alkanolamines, for example mono-, di- and triethanolamine, and primary, secondary or tertiary $C_{1-4}$ alkylamines and also glucamines. The neutralization bases are preferably used in the form of 5 to 55% by weight aqueous solutions, 5 to 25% by weight aqueous sodium hydroxide solutions being preferred.

After neutralization, the sulfation products may be bleached in known manner by addition of hydrogen peroxide or sodium hypochlorite solution. 0.2 to 2% by weight of hydrogen peroxide, expressed as 100% substance, or corresponding quantities of sodium hypochlorite are used, based on the solids content of the solution of sulfation products. The pH value of the solutions may be kept constant using suitable buffers, for example sodium phosphate or citric acid. In addition, preservation, for example with formaldehyde solution, p-hydroxybenzoate, sorbic acid or other known preservatives, is advisable for stabilization against bacterial contamination.

Conditioning Formulations

The formulations according to the invention preferably contain the sulfated polyol fatty acid esters in the form of their mono- and/or diesters and mono- and/or disulfates. Examples of preferred sulfated polyol fatty acid esters are mentioned in the following:

Trimethylol propane monotallow fatty acid ester monosulfate sodium salt corresponding to formula (I), in which $R^1CO$ is an acyl radical containing 16 to 18 carbon atoms, $R^2$ is hydrogen, $R^3$ is hydrogen, n=2, m=0 and X is sodium.

Trimethylol propane ditallow fatty acid ester monosulfate sodium salt corresponding to formula (I), in which $R^1CO$ is an acyl radical containing 16 to 18 carbon atoms, $R^2$ is an $OCR^1$ group, $R^3$ is hydrogen, n=2, m=0 and X is sodium.

Trimethylol propane monotallow fatty acid ester disulfate disodium salt corresponding to formula (I), in which $R^1CO$ is an acyl radical containing 16 to 18 carbon atoms, $R^2$ is an $SO_3X$ group, $R^3$ is hydrogen, n=2, m=0 and X is sodium.

Pentaerythritol monotallow fatty acid ester monosulfate sodium salt corresponding to formula (I), in which $R^1CO$ is an acyl radical containing 16 to 18 carbon atoms, $R^2$ is hydrogen, $R^3$ is hydrogen, n=1, m=0 and X is sodium.

Pentaerythritol ditallow fatty acid ester monosulfate sodium salt corresponding to formula (I), in which $R^1CO$ is an acyl radical containing 16 to 18 carbon atoms, $R^2$ is an $R^1CO$ group, $R^3$ is hydrogen, n=1, m=0 and X is sodium.

Pentaerythritol monotallow fatty acid ester disulfate disodium salt corresponding to formula (I), in which $R^1CO$ is an acyl radical containing 16 to 18 carbon atoms, $R^2$ is an $SO_3X$ group, $R^3$ is hydrogen, n=1, m=0 and X is sodium.

Pentaerythritol ditallow fatty acid ester disulfate disodium salt corresponding to formula (I), in which $R^1CO$ is an acyl radical containing 16 to 18 carbon atoms, $R^2$ is an $R^1CO$ group, $R^3$ is a $CH_2OSO_3X$ group, n=1, m=0 and X is sodium.

The nitrogen-free anionic conditioning formulations according to the invention may normally contain the sulfated polyol fatty acid esters corresponding to formula (I) in quantities of 1 to 70% by weight and preferably in quantities of 10 to 50% by weight, based on the solids content of the formulations. The formulations themselves are generally marketed in the form of water-containing concentrates with a solids content of 30 to 70% by weight or in the form of flakes. In addition to the sulfated polyol fatty acid esters mentioned, they may contain other typical auxiliaries and additives in the usual quantities, including for example dispersants, perfumes and viscosity regulators.

Commercial Applications

The sulfated polyol fatty acid esters present in the conditioning formulations according to the invention are ecotoxicologically very safe and provide textile materials and also leather and paper with a pleasant soft feel. Accordingly, the formulations according to the invention may be used, for example, for the continuous or discontinuous treatment of textiles.

Accordingly, the present invention also relates to the use of the sulfated polyol fatty acid esters for the production of conditioners and fabric softeners in which they may be present in quantities of 1 to 70% by weight, preferably in quantities of 10 to 50% by weight and more preferably in quantities of 15 to 30% by weight, based on the conditioner/softener as a whole. In addition, the conditioners/softeners according to the invention may contain other typical additives such as, for example, surfactants, emulsifiers, synthetic resins, catalysts and optical brighteners.

EXAMPLES

I. Production Example a) Production of pentaerythritol distearic acid ester. 1200 g (4.4 moles) of technical stearic acid (EDEN-OR® ST1, a product of Henkel KGaA, Düsseldorf, FRG), 300 g (2.2 moles) of pentaerythritol and 5 g of tin oxalate (catalyst) were heated at 200° C. in a distillation apparatus consisting of a 2 liter three-necked flask equipped with a thermometer, gas inlet pipe and distillation bridge until the theoretical quantity of water had separated. 1430 g of a light yellow solid were obtained. The product had the following characteristic data: Acid value: 0.8 Hydroxyl value: 150 Saponification value: 179 b) Production of pentaerythritol distearate monosulfate sodium salt. 3470 g (5 moles) of the pentaerythritol ester from a) were reacted with gaseous sulfur trioxide at 95° C. in a continuous falling-film reactor (length 120 cm, cross-section 1 cm, educt throughput 600 g/h) equipped with a jacket cooling system and a lateral inlet for $SO_3$ gas. The ratio of ester to $SO_3$ was 1:1.13. The sulfur trioxide had been driven out by heating from a corresponding quantity of 65% by weight oleum, diluted with nitrogen to a concentration of 5% by volume and contacted with the ester film through a nozzle.

The crude sulfation product was stirred with a 37% by weight sodium hydroxide solution into a 1% by weight solution of sodium triphosphate and neutralized at pH 6.5 to 8.

Characteristic Data of the Product

Anionic surfactant content (Epton method): 10.0% by weight (MW=850.1) Unsulfonated: 14.8% by weight Sodium sulfate: 0.1% by weight Water: 75.0% by weight The anionic surfactant content (WAS) and the unsulfonated components (US) were determined by the DGF-Einheitsmethoden, Stuttgart 1950–1984, H-III-10 and G-II-6b.

II. Application Example

The conditioning effect of formulation (A) according to the invention was determined by the padding method by forced application to a cotton fabric. The softening performance was determined by feel by a panel of 6 examiners. A commercial conditioner based on a fatty acid polyamine condensate (B) was used for comparison. The parameters were as follows: Concentration: 30 g/l of the 20% by weight products Material: Terry cloth Liquor uptake: approx. 80% by weight, based on dry fabric Drying: 3 mins. at 130° C.

The results are set out in Table 1.

TABLE 1

| Determination of softening performance | |
|---|---|
| Softener | Feel Score |
| A | 5.0 |
| B | 5.0 |

Legend

Feel score 1=hard Feel score 6=very soft

We claim:

1. A nitrogen-free anionic conditioning or fabric-softening formulation comprising (A) from about 10 to about 70% by weight of at least one sulfated polyol fatty acid ester of the formula

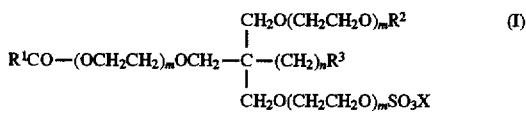 (I)

in which R¹CO is a linear or branched, saturated or unsaturated acyl radical containing 6 to 22 carbon atoms, R² represents hydrogen, an OCR¹ group or an SO₃X group, R³ is hydrogen or an (OCH₂CH₂)ₘOR² group, n is 0 or a number of 1 to 5, m is 0 or a number of 1 to 10, and X is an alkali metal, alkaline earth metal, ammonium, alkylammonium, alkanolammonium or glucammonium ion; and (B) at lease one additive selected from the group consisting of a dispersant, a perfume, a viscosity regulator, another surfactant, an emulsifier, a synthetic resin, a catalyst, and an optical brightener;

wherein the above percentages am based on the solids content of the formulation.

2. The formulation of claim 1 which is in the form of a water-containing concentrate.

3. The formulation of claim 2 which contains a solids content of from about 30 to about 70% by weight.

4. The formulation of claim 1 which is a solid composition in the form of flakes.

5. The formulation of claim 1 wherein component (A) is present in from about 10 to about 50% by weight.

6. The formulation of claim 1 wherein component (A) is present in from about 15 to about 30% by weight.

7. The formulation of claim 1 wherein in formula I in component (A), R¹CO is an acyl radical containing 16 to 18 carbon atoms, R² is hydrogen, R³ is hydrogen, n=2, m=0 and X is sodium.

8. The formulation of claim 1 wherein in formula I an component (A), R¹CO is an acyl radical containing 16 to 18 carbon atoms, R² is an OCR¹ group, R³ is hydrogen, n=2, m=0 and X is sodium.

9. The formulation of claim 1 wherein in formula I in component (A), R¹CO is an acyl radical containing 16 to 18 carbon atoms, R² is an SO₃X group, R³ is hydrogen, n=2, m=0 and X is sodium.

10. The formulation of claim 1 wherein in formula I in component (A), R¹CO is an acyl radical containing 16 to 18 carbon atoms, R² is hydrogen, R³ is hydrogen, n=1, m=0 and X is sodium.

11. The formulation of claim 1 wherein in formula I in component (A), R¹CO is an acyl radical containing 16 to 18 carbon atoms, R² is an R¹CO group, R³ is hydrogen, n=1, m=0 and X is sodium.

12. The formulation of claim 1 wherein in formula I in component (A), R¹CO is an acyl radical containing 16 to 18 carbon atoms, R² is an SO₃X group, R³ is hydrogen, n=1, m=0 and X is sodium.

13. The formulation of claim 1 wherein in formula I in component (A), R¹CO is an acyl radical containing 16 to 18 carbon atoms, R² is an R¹CO group, R³ is a CH₂OSO₃X group, n=1, m=0 and X is sodium.

14. A method for conditioning textiles comprising contacting said textiles with a conditioning or fabric-softening quantity of at least one sulfated polyol fatty acid ester of the formula

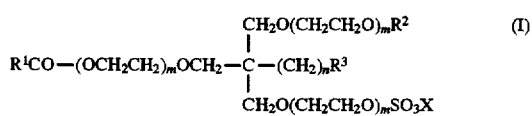 (I)

in which R¹CO is a linear or branched, saturated or unsaturated acyl radical containing 6 to 22 carbon atoms, R² represents hydrogen, an OCR¹ group or an SO₃X group, R³ is hydrogen or an (OCH₂CH₂)ₘOR² group, n is 0 or a number of 1 to 5, m is 0 or a number of 1 to 10, and X is an alkali metal, alkaline earth metal, ammonium, alkylammonium, alkanolammonium or glucammonium ion.

15. A method for conditioning leather comprising contacting the leather with a conditioning quantity of at least one sulfated polyol fatty acid ester of the formula

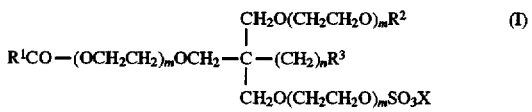 (I)

in which R¹CO is a linear or branched, saturated or unsaturated acyl radical containing 6 to 22 carbon atoms, R² represents hydrogen, an OCR¹ group or an SO₃X group, R³ is hydrogen or an (OCH₂CH₂)ₘOR² group, n is 0 or a number of 1to 5, m is 0 or a number of 1 to 10, and X is an alkali metal, alkaline earth metal, ammonium, alkylammonium, alkanolammonium or glucammonium ion.

16. A method for conditioning paper comprising contacting the paper with a conditioning quantity of at least one sulfated polyol fatty acid ester of the formula

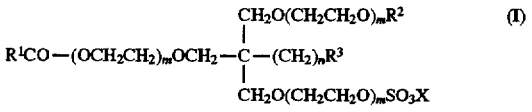 (I)

in which R¹CO is a linear or branched, saturated or unsaturated acyl radical containing 6 to 22 carbon atoms, R² represents hydrogen, an OCR¹ group or an SO₃X group, R³ is hydrogen or an (OCH₂CH₂)ₘOR² group, n is 0 or a number of 1 to 5, m is 0 or a number of 1 to 10; and X is an alkali metal, alkaline earth metal, ammonium, alkylammonium, alkanolammonium or glucammonium ion.

17. The method of claim 14 wherein in formula I, R¹CO is an acyl radical containing 16 to 18 carbon atoms.

18. The method of claim 15 wherein in formula I, R¹CO is an acyl radical containing 16 to 18 carbon atoms.

19. The method of claim 16 wherein in formula I, R¹CO is an acyl radical containing 16 to 18 carbon atoms.

* * * * *